United States Patent [19]

Schulz

[11] Patent Number: 5,176,621
[45] Date of Patent: Jan. 5, 1993

[54] CASTING AND SPLINTING PRODUCT HAVING MULTIPLE PLASTER SETTING RATES

[75] Inventor: George A. Schulz, Lawrence, Kans.

[73] Assignee: M-Pact Worldwide Management Corporation, Eudora, Kans.

[21] Appl. No.: 692,531

[22] Filed: Apr. 29, 1991

[51] Int. Cl.⁵ .............................................. A61F 5/04
[52] U.S. Cl. ...................................................... 602/8
[58] Field of Search ................ 128/89, 90, 91 R, 155, 128/156, 157, 161, 162, 165, 166; 602/8, 5, 6, 7

[56] References Cited

U.S. PATENT DOCUMENTS

| | | | |
|---|---|---|---|
| 3,900,024 | 8/1975 | Lauber et al. | 128/91 R |
| 3,923,049 | 12/1975 | Lauber et al. | 128/91 R |
| 3,935,355 | 1/1976 | Kuhn | 128/90 X |
| 4,060,075 | 11/1977 | Bloma et al. | 128/90 |
| 4,126,130 | 11/1978 | Cowden et al. | 128/156 X |
| 4,235,450 | 3/1981 | Smith | 128/91 R |
| 4,454,874 | 6/1984 | Monnier | 128/91 R |
| 4,968,542 | 11/1990 | Gosper et al. | 128/90 X |
| 4,989,593 | 2/1991 | Campagna et al. | 128/91 RX |
| 5,027,803 | 7/1991 | Scholz et al. | 128/91 RX |

Primary Examiner—Robert A. Hafer
Assistant Examiner—Brian E. Hanlon
Attorney, Agent, or Firm—Shook, Hardy & Bacon

[57] ABSTRACT

A casting blank for forming orthopedic casts is provided with two layers of plaster splints having different setting rates or times. The plaster splint layer disposed on a lower sheet of the casting blank sets more slowly than the layer disposed on an upper sheet of the blank. The quicker setting upper plaster splint layer rapidly immobilizes the injured body part, while the slower setting lower splint layer results in greater final cure strength and insulates the body part from the heat generated by the upper layer to prevent burning of the skin surface. The slower setting lower splint layer adapts more completely to the contours of the body portion to increase patient comfort.

31 Claims, 1 Drawing Sheet

CASTING AND SPLINTING PRODUCT HAVING MULTIPLE PLASTER SETTING RATES

BACKGROUND OF THE INVENTION

This invention relates generally to orthopedic plaster casts and, more particularly, to an improved plaster casting blank for use in preparing such casts.

Plaster casts such as those disclosed in U.S. Pat. Nos. 3,923,049 and 3,900,024 utilize a plurality of plaster splints disposed between two sheets of deformable water permeable material to form the casting blank. When wetted, the casting blank may be formed around a portion of a body and, upon curing of the plaster, a cast is thereby provided.

Casting blanks of the type described in the aforementioned patents represent a significant advance over the time consuming method of preparing casts by wrapping individually moistened plaster splints about the injured body portion. Because of the ease with which casting blanks may used to prepare casts, they have been widely used to prepare orthopedic casts. Such casting blanks are particularly well suited for use on an emergency basis, such as to immobilize broken bones at the scene of an accident or in a hospital emergency room prior to the final cast being applied.

It is desirable for the casting blanks of the type described above to have a rapid setting time to quickly immobilize the broken bone or other trauma to prevent further injury which might result from movement of the injured body portion. However, great care must be exercised in formulating the plaster within the blank to ensure that the amount of heat generated by the exothermic chemical reaction which leads to hardening of the plaster is less than that which would burn the patient's skin. The amount of heat generated by the chemical reaction generally increases as the setting rate of the plaster within the casting blank increases. As a result, casting blanks are often formulated to cure more slowly than would otherwise be desired to ensure that the temperatures generated remain within safe levels.

Another disadvantage of a rapid setting time for a casting blank is the decreased strength of the resulting cast. In general, the strength of the cast decreases as the setting time of the plaster decreases. Casts formed from rapidly setting plasters may lack the durability needed for other than short term use. Replacement of such casts is thus necessitated, with the attendant expense and discomfort for the patient. Moreover, conventional rapidly setting casting blanks may contribute to patient discomfort a the blanks have less opportunity to conform to the anatomical features of the underlying body part before hardening.

A need has thus developed for a rapidly setting casting blank which may be used to form a high strength cast to quickly immobilize an injury with reduced risk of burning the patient's skin and which provides greater patient comfort than achieved by conventional casting blanks.

SUMMARY OF THE INVENTION

It is an object of this invention to provide a casting blank for use in forming a quick setting orthopedic cast which presents lower temperatures in skin contact zones to reduce the risk of burning the skin underlying the body portion to which the blank is applied.

It is also an object of this invention to provide a casting blank which may be used to quickly immobilize an injured body portion by forming a cast which sets rapidly but which also possesses high strength characteristics so that it is more durable yet lighter in weight than casts formed from conventional rapidly setting casting blanks.

It is a further object of this invention to provide a casting blank which provides rapid immobilization of an injured body part but which also adapts more completely to the contours of the body part to which it is applied in order to provide a better fit and thereby increase patient comfort.

To achieve these and other objects of the invention, a casting blank having at least two different plaster setting zones is provided for use in forming a plaster cast for a portion of a body. The casting blank comprises:

a first sheet of deformable water permeable material;

a first layer of dry plaster material disposed on said first sheet of deformable water permeable material and having a preselected setting time after exposure to water;

a second layer of dry plaster material disposed on said first layer of plaster material and having a shorter setting time after exposure to water than the setting time of the first layer of plaster material; and a second sheet of deformable water permeable material overlying said second layer of plaster material, said first and second sheets being joined together to hold said layers of plaster material therebetween.

The different layers of plaster material in the casting blank form both a fast setting zone for rapid immobilization of the injury and a slow setting zone which maintains safe temperature levels in skin contact areas and which provides greater strength and comfort than would otherwise be obtainable.

BRIEF DESCRIPTION OF THE DRAWINGS

In the accompanying drawings which form a part of the specification and are to be read in conjunction therewith and in which like reference numerals are used to indicate like parts in the various views.

DETAILED DESCRIPTION OF THE INVENTION

Figure 1:
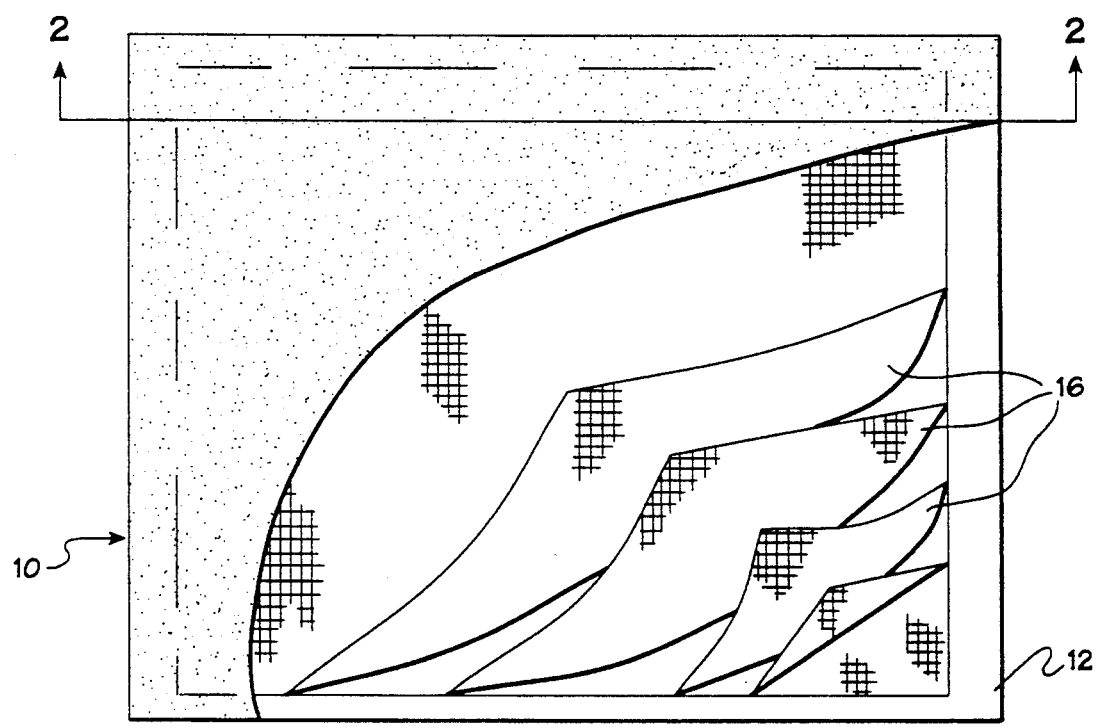
FIG. 1 is a top plan view of a casting blank made according to the teachings of the present invention, with a portion broken away and other portions pealed back to illustrate details of construction.
Figure 2:
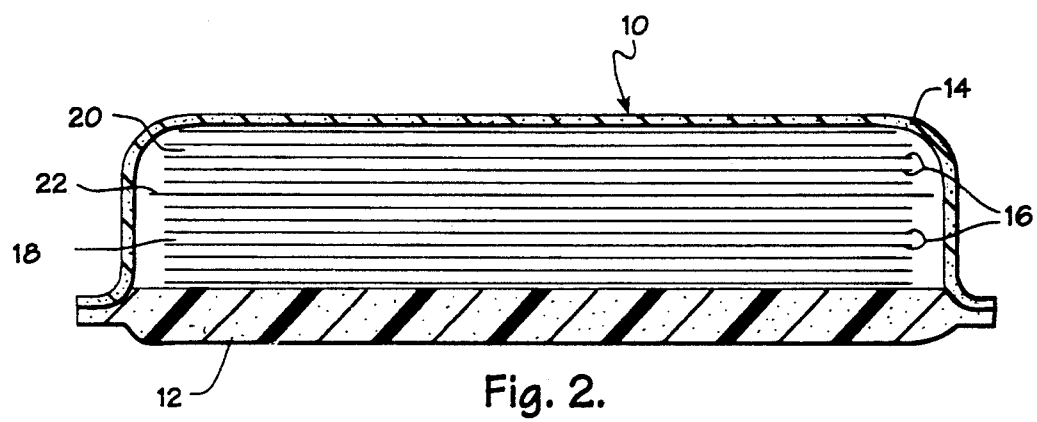
FIG. 2 is a side elevational view of the casting blank taken in vertical cross-section along line 2—2 of FIG. 1.

Referring now to the drawings in more detail, a casting blank of the present invention is represented broadly by the numeral 10. As best seen in FIG. 2, casting blank 10 comprises a first or lower sheet 12, a second or upper sheet 14 joined at its peripheral edge with the peripheral edges of the lower sheet, and a plurality of layers of plaster splints 16 enclosed between the lower and upper sheets 12 and 14.

Lower sheet 12 is adapted to be placed closest to the body of the wearer of the cast formed from casting blanks 10. Lower sheet 12 comprises a water permeable deformable material, preferably one having a cellular construction and a nonaffinity for absorbing moistened or wetted plaster. Foam, such as made from polyurethane, is an example of a suitable material for use in constructing lower sheet 12.

Upper sheet 14 also comprises a water permeable deformable material, but is preferably of a fibrous construction having an affinity for absorption of wetted plaster. Flannel cloth is an example of a suitable material for upper sheet 14.

The plaster splints 16 which are disposed between the upper and lower sheets comprise layers of gauze cloth impregnated with dry plaster ingredients. The term "plaster splints" as used herein is intended to include any dry plaster or plaster-like material which will harden after water has been added, impregnated on or associated with a carrier such as the gauze cloth or other porous material.

The plaster splints 16 provided in the casting blank of this invention are advantageously divided into two or more zones. In the illustrated embodiment, a lower zone 18 and an upper zone 20 are provided, the separation between the zones being provided by a layer of reinforcing material 22. The layers of plaster splints 16 in lower zone 18 are disposed on the lower sheet 12, with the splint layers in upper zone 20 being disposed between the upper sheet 14 and the reinforcing material 22 which is applied on top of the splints of lower zone 18.

The reinforcing layer 22 is formed from porous material which will absorb or incorporate moistened plaster from the adjacent splints 16 to impart added strength to the formed cast. Nylon mesh is particularly suited for this purpose but polypropylene or polyester mesh or other materials may also be used. The reinforcing layer 22 may also be placed between splints 16 within upper zone 20 or lower zone 18 rather than being positioned between such zones.

The plaster splints 16 in lower zone 18 are formulated to set at a slower rate after exposure to water than the splints in upper zone 20, with the differential between the setting times being chosen to suit particular applications. As used herein, the terms "set" and "setting" are intended to refer to the point at which the chemical reaction initiated by wetting of the plaster is complete enough to impart rigidity to the blank 10.

In one preferred embodiment of the invention, the setting time of the plaster splints in the lower zone 18 of the blank 10 is within the range of approximately three to six minutes following saturation with room temperature water, with the setting time of the splints in the upper zone 20 being within the range of approximately two to four minutes following such saturation. The temperatures reached within the upper zone 20 during setting fall within the range of approximately 95° to 115° F. after room temperature water has been added to the blank. The temperature generated by the plaster splints within the lower zone is within the range of approximately 80° to 90° F., although the actual temperature reached within the lower zone may be 5° to 10° F. higher due to absorption of heat from the upper zone.

It will be appreciated that the actually setting rate of the plaster splints within the lower zone may be accelerated somewhat by the heat absorbed from the upper zone. It is also to be understood that an aspect of the invention resides in the use of two or more zones having different setting rates. The number of zones and the setting rates or times may be varied from that described and still fall within the scope of the invention.

In order to achieve the desired setting times and temperatures for the plaster splints 16, various additives may be used in the plaster formulation. The setting time of the plaster may be decreased by the addition of various accelerators to the plaster formulation. Potassium sulfate ($K_2SO_4$) is the preferred accelerator used in the present invention, although other accelerators such as hydrated calcium sulfate ($CaSO_4 \cdot 2H_2O$) may also be used. It will be appreciated that the setting and curing rate may also be affected by conditions of temperature and pressure to which the gypsum used in the plaster formulation has been subjected.

The number of plaster splints 16 in the respective zones 18 and 20 may be the same or different, the total number of splints being selected to provide the strength required for the resulting cast. In general, fewer splints are required in comparison to conventional rapidly setting casting blanks because of the greater strength of the cast formed from blank 10. In one embodiment of the invention, the lower zone contains at least one and one-half times the number of splints as the upper zone. The total number of plaster splints required depends upon the intended application of the casting blank 10. For example, up to twenty splints 16 may be required to achieve the necessary cast strength to support large body portions, such as a leg.

Likewise, the size and configuration of the casting blank 10 may be varied from that illustrated to suit particular applications. For example, if the casting blank is intended to provide a lumbar or neck support, it will be more elongated than the blank schematically illustrated. In other applications, it may be desired to provide a continuous roll of the casting blank so that a length of the blank may simply be cut from the roll when needed.

The casting blank 10 is made by cutting the lower sheet 12 to the size and shape desired. The upper sheet is then sized to overlay the lower sheet 12 and is initially stitched or otherwise secured to the lower sheet along one of the peripheral edges. The reinforcing material 22 and the desired number of plaster splints 16 for plaster zones 18 and 20 are placed between the upper and lower sheets, the splints and reinforcing material being sized so that the peripheral edges of the sheets extend beyond the peripheral edges of the splints and reinforcing material. The three open sides of the blank are then secured to complete the casting blank. If desired, a centrally positioned stitch may also be provided to further secure the casting blank. Instead of securing the upper and lower sheets at their peripheral edges, the sheets may instead be secured together in other suitable fashions, such as by stitching which extends through the plaster splints 16.

In use, the casting blank 10 is submerged in water to initiate the exothermic chemical reaction which results in hardening of the plaster. In general, the blank is submerged until the upper and lower sheets 12 and 14 become saturated and the dry plaster in the splints becomes soft, which time period may be up to approximately 20 seconds. The blank is then removed from the water and the excess moisture pressed from the blank. The blank is then applied to the injured body portion by forming and smoothing to conform the blank to the body part surface. The plaster splints 16 then cure and harden to form the rigid cast. The upper sheet 14 and the layer of reinforcing material 22, by incorporating a quantity of wetted plaster, provide added strength to the resulting cast, while the cellular lower sheet 12 retains its resiliency and provides a measure of patient comfort.

It will be appreciated that the provision of two zones of plaster splints having different setting rates or times provides important advantages not found in conventional casting blanks. Upon application of the wetted casting blank 10 to the injury, the upper zone 20 quickly immobilizes the injured body part by rapidly setting to form a hard shell. The lower zone 18, meanwhile, insulates and protects the body part by absorbing heat from the upper zone to prevent burning of the underlying skin. The heat sink effect of the lower zone allows the faster setting plaster formulation to be used for the upper zone, thereby significantly decreasing the time required to immobilize the injury.

In the preferred embodiment of the invention, the upper zone 20 sets within the range of approximately two to four minutes after room temperature water has been added and reaches a temperature in the range of approximately 95° to 115° F. The lower zone 18 sets within the range of approximately three to six minutes after saturation with room temperature water. The temperature reached within the lower zone 18 is approximately 85° to 100° F., with approximately 5° to 10° F. of that temperature being attributable to heat transferred from the upper zone. The heat generated by the lower zone 18 itself is preferably such that the temperature within the lower zone would reach 80° to 90° F. absent heat transfer from the upper zone 20.

The insulating effect of the lower zone 18 allows the use of water warmer than room temperature to accelerate the setting rate if desired, at a greatly reduced risk of burning the patient's skin when the casting blank 10 is applied thereto. The casting blank may thus be used to prepare a cast with less potential risk to the recipient than is associated with attempts at accelerating the curing rate of conventional blanks. Moreover, in some applications such as emergency usage of the blank, it may in fact be desirable to accelerate the setting rate of the blank 10. The use of two zones 18 and 20 readily permits the use of warmer water for such purpose at a greatly reduced risk of burning the patient.

In addition to the rapid immobilization provided by the rapidly setting upper zone 20, the provision of slower setting lower zone 18 provides a better fit by allowing a greater opportunity for the casting blank 10 to adapt to the underlying contours of the body portion before complete hardening occurs. Patient comfort is significantly improved by this extended break-in period even though the outer portion of the cast has rapidly hardened to provide the immobilizing structural support which prevents further injury which would result from movement of the injured body part.

The slower setting rate of the lower zone 18 significantly increases the overall strength of the resulting fully cured cast, with the provision of reinforcing layer 22 within the casting blank 10 further increasing the strength of the cast. The cast made with the casting blank 10 is thus stronger and more durable than casts formed from conventional quick setting casting blanks, thereby allowing the cast to be worn for a longer period without need of replacement and the attendant cost and discomfort for the patient.

Because of the higher strength of a cast formed from casting blank 10, fewer layers of plaster splints 16 are required within the blank. This reduction in the number of splints 16 decreases the materials cost for making blank 10 and the blanks may be shipped at lesser expense because of their lighter weight. The use of fewer splints 16 also greatly increases patient comfort since the resulting cast is lighter and less bulky than casts formed from conventional quick setting casting blanks.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without department from the scope thereof, it is to be understood that all matter herein set forth or shown in the accompanying drawings is to be interpreted as illustrative and not in a limiting sense.

Having thus described the invention, what is claimed is:

1. A casting blank for use in forming a plaster cast for a portion of a body, said blank comprising:
   first sheet of deformable water permeable material;
   a first layer of dry plaster material disposed on said first sheet of deformable water permeable material and having a preselected setting time after exposure to water;
   a second layer of dry plaster material disposed on said first layer of plaster material and having a shorter setting time after exposure to water than the setting time of the first layer of plaster material; and
   a second sheet of deformable water permeable material overlying said second layer of plaster material, said first and second sheets being joined together to hold said layers of plaster material therebetween.

2. The casting blanks of claim 1, wherein said first sheet of deformable water permeable material is adapted to be placed closest to the body of the wearer of said cast.

3. The casting blank of claim 2, wherein the setting time of said first layer of plaster material is within the rang of approximately three to six minutes.

4. The casting blank of claim 3, wherein the setting time of said second layer of plaster material is within the range of approximately two to four minutes.

5. The casting blank of claim 4, wherein one of said first and second sheets of deformable water permeable material comprises a fibrous material having an affinity for moistened plaster.

6. The casting blank of claim 5, wherein said first sheet of deformable water permeable material comprises a cellular material having a nonaffinity for moistened plaster.

7. The casting blank of claim 4, wherein said first and second layers of dry plaster material comprise porous sheets impregnated with dry plaster.

8. The casting blank of claim 2, including a sheet of reinforcing material disposed between or within said first and second layers of dry plaster material.

9. The casting blank of claim 8, wherein said sheet of reinforcing material comprises a porous material having an affinity for moistened plaster.

10. A casting blank for use in forming a plaster cast for a portion of a body, said blank comprising:
   a first sheet of deformable water permeable material having nonaffinity for moistened plaster,
   a first layer of dry plaster material disposed on said first sheet of deformable water permeable material and formulated to generate a temperature of less than approximately 90° F. during setting at room temperature after exposure to room temperature water;
   a second layer of dry plaster material disposed on said first layer of plaster material and formulated to generate a higher temperature upon setting after exposure to water than that generated by said first layer of plaster material; and a second sheet of deformable water permeable material overlying said second layer of plaster material, said first and second sheets being joined together to hold said layers of plaster material therebetween.

11. The casting blank of claim 10, wherein said first sheet of deformable water permeable material is adapted to be placed closest to the body of the wearer of said cast and said first layer of plaster material comprises multiple layers of plaster splints and has a setting temperature within the range of approximately 80° to 90° F.

12. The casting blank of claim 10, wherein said second layer of plaster material comprises multiple layers of plaster splints and has a setting temperature within the range of approximately 95° to 115° F.

13. The casting blank of claim 12, wherein said first layer of plaster material has a setting time within the range of approximately three to six minutes.

14. The casting blank of claim 13, wherein said second layer of plaster material has a setting time within the range of approximately two to four minutes.

15. The casting blank of claim 11, wherein one of said first and second sheets of deformable water permeable material comprises a cellular material having a nonaffinity for moistened plaster.

16. The casting blank of claim 13, wherein the other of said first and second sheets of deformable water permeable material comprises a fibrous material having an affinity for moistened plaster.

17. The casting blank of claim 15, wherein said first sheet of deformable water permeable material comprises said cellular material.

18. The casting blank of claim 11, including a sheet of reinforcing material disposed between or within said first and second layers of dry plaster material.

19. The casting blank of claim 18, wherein said sheet of reinforcing material comprises a porous material having an affinity for moistened plaster.

20. A casting blank comprising:
a first sheet of deformable water permeable material;
a second sheet of deformable water permeable material overlying said first sheet of deformable water permeable material;
first and second layers of dry plaster material sandwiched between said first and second sheets of deformable water permeable material,
said first layer of plaster material having a preselected setting time after exposure to water and being disposed between the first sheet of deformable water permeable material and said second layer of plaster material,
said second layer of plaster material having a shorter setting time after exposure to water than said setting time of said first layer of plaster material, said second layer of plaster material being disposed between said first layer of plaster material and said second sheet of deformable water permeable material,
said first and second sheets of deformable water permeable material being joined together to hold said layers of plaster material therebetween.

21. The casting blank of claim 20, wherein said first layer of plaster material has a setting temperature within the range of approximately 80° to 90° F.

22. The casting blank of claim 20, wherein said second layer of plaster material has a setting temperature within the range of approximately 95° to 115° F.

23. The casting blank of claim 20, wherein said first layer of plaster material has a setting time within the range of approximately three to six minutes.

24. The casting blank of claim 20, wherein said second layer of plaster material has a setting time within the range of approximately two to four minutes.

25. The casting blank of claim 20, wherein said first sheet of deformable water permeable material comprises a cellular material having a nonaffinity for moistened plaster.

26. The casting blank of claim 25, wherein said second sheet of deformable water permeable material comprises a fibrous material having an affinity for moistened plaster.

27. The casting blank of claim 20, wherein each of said layers of plaster material comprises multiple layers of plaster splints.

28. The casting blank of claim 21, including a sheet of reinforcing material disposed between or within said first and second layers of dry plaster material.

29. The casting blank of claim 28, wherein said sheet of reinforcing material comprises a porous material having an affinity for moistened plaster.

30. A method of constructing a casting blank from which a plaster cast for a portion of a body may be formed, said method comprising the steps of:
providing first and second sheets of deformable water permeable material;
placing a quantity of a first plaster splint material on said first sheet of deformable water permeable material to form a first plaster zone characterized by a preselected setting rate upon exposure to water;
placing a quantity of a second plaster splint material on said first plaster zone to form a second plaster zone characterized by a faster setting rate upon exposure to water than said setting rate of said first zone; and
joining said first and second sheets together to hold said first and second plaster splint materials therebetween.

31. The method of claim 30, including the step of providing within or between said first and second plaster zones a layer of reinforcing material having a higher strength than said plaster splint material.

* * * * *